United States Patent
Lovett

(10) Patent No.: US 8,239,021 B2
(45) Date of Patent: *Aug. 7, 2012

(54) CARDIAC PACING SYSTEM FOR PREVENTION OF VENTRICULAR FIBRILLATION AND VENTRICULAR TACHYCARDIA EPISODE

(75) Inventor: Eric G. Lovett, Mendota Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/816,088

(22) Filed: Jun. 15, 2010

(65) Prior Publication Data

US 2010/0249866 A1 Sep. 30, 2010

Related U.S. Application Data

(62) Division of application No. 11/380,148, filed on Apr. 25, 2006, now Pat. No. 7,742,814, which is a division of application No. 09/569,295, filed on May 13, 2000, now Pat. No. 7,039,461.

(51) Int. Cl.
*A61N 1/00* (2006.01)
(52) U.S. Cl. ........................................................ 607/14
(58) Field of Classification Search ................ 607/9, 14; 600/509, 515
See application file for complete search history.

(56) References Cited

U.S. PATENT DOCUMENTS

| | | | |
|---|---|---|---|
| 3,857,399 A | 12/1974 | Zacouto | |
| 4,030,510 A | 6/1977 | Bowers | |
| 4,059,116 A | 11/1977 | Adams | |
| 4,163,451 A | 8/1979 | Lesnick et al. | |
| 4,208,008 A | 6/1980 | Smith | |
| RE30,387 E | 8/1980 | Denniston, III et al. | |
| 4,432,360 A | 2/1984 | Mumford et al. | |
| 4,485,818 A | 12/1984 | Leckrone et al. | |
| 4,503,857 A | 3/1985 | Boute et al. | |
| 4,549,552 A | 10/1985 | Groch et al. | |
| 4,554,922 A | 11/1985 | Prystowsky et al. | |
| 4,556,063 A | 12/1985 | Thompson et al. | |
| 4,562,841 A | 1/1986 | Brockway et al. | |
| 4,596,255 A | 6/1986 | Snell et al. | |
| 4,680,708 A | 7/1987 | Ambos et al. | |
| 4,712,556 A | 12/1987 | Baker, Jr. | |
| 4,787,389 A | 11/1988 | Tarjan | |
| 4,791,936 A | 12/1988 | Snell et al. | |

(Continued)

FOREIGN PATENT DOCUMENTS

EP 0033418 A1 8/1981

(Continued)

OTHER PUBLICATIONS

"U.S. Appl. No. 11/759,394, Final Office Action mailed Apr. 28, 2011", 7 pgs.

(Continued)

*Primary Examiner* — Mark W Bockelman
(74) *Attorney, Agent, or Firm* — Schwegman, Lundberg & Woessner, P.A.

(57) ABSTRACT

A cardiac pacing system preventing short-long-short pacing sequences. The system providing pacing pulses where necessary. The system having dynamic event window generation to adapt to changes in heart rate. The event window adaptable to process a number of intervals. The system including provisions for other inputs, such as sensor and morphology detection. The system adaptable for single mode and dual mode applications. The system also applicable to long pause prevention in atrial pacing and ventricular pacing.

15 Claims, 8 Drawing Sheets

U.S. PATENT DOCUMENTS

| | | |
|---|---|---|
| 4,809,697 A | 3/1989 | Causey, III et al. |
| 4,830,006 A | 5/1989 | Haluska et al. |
| 4,856,523 A | 8/1989 | Sholder et al. |
| 4,860,749 A | 8/1989 | Lehmann |
| 4,869,252 A | 9/1989 | Gilli |
| 4,890,617 A | 1/1990 | Markowitz et al. |
| 4,905,697 A | 3/1990 | Heggs et al. |
| 4,917,115 A | 4/1990 | Flammang et al. |
| 4,920,965 A | 5/1990 | Funke et al. |
| 4,928,688 A | 5/1990 | Mower |
| 4,932,406 A | 6/1990 | Berkovits |
| 4,940,054 A | 7/1990 | Grevis et al. |
| 4,941,471 A | 7/1990 | Mehra |
| 4,944,298 A | 7/1990 | Sholder |
| 4,944,928 A | 7/1990 | Grill et al. |
| 4,945,909 A | 8/1990 | Fearnot et al. |
| 4,972,834 A | 11/1990 | Begemann et al. |
| 4,998,974 A | 3/1991 | Aker |
| 5,002,052 A | 3/1991 | Haluska |
| 5,012,814 A | 5/1991 | Mills et al. |
| 5,042,480 A | 8/1991 | Hedin et al. |
| 5,047,930 A | 9/1991 | Martens et al. |
| 5,077,667 A | 12/1991 | Brown et al. |
| 5,085,215 A | 2/1992 | Nappholz et al. |
| 5,101,824 A | 4/1992 | Lekholm |
| 5,107,850 A | 4/1992 | Olive |
| 5,113,869 A | 5/1992 | Nappholz et al. |
| 5,127,401 A | 7/1992 | Grevious et al. |
| 5,127,404 A | 7/1992 | Wyborny et al. |
| 5,129,394 A | 7/1992 | Mehra |
| 5,133,350 A | 7/1992 | Duffin |
| 5,139,020 A | 8/1992 | Koestner et al. |
| 5,144,949 A | 9/1992 | Olson |
| 5,156,147 A | 10/1992 | Warren et al. |
| 5,156,154 A | 10/1992 | Valenta, Jr. et al. |
| 5,161,527 A | 11/1992 | Nappholz et al. |
| 5,179,945 A | 1/1993 | Van Hofwegen et al. |
| 5,179,949 A | 1/1993 | Chirife |
| 5,183,040 A | 2/1993 | Nappholz et al. |
| 5,184,614 A | 2/1993 | Collins et al. |
| 5,188,105 A | 2/1993 | Keimel |
| 5,188,106 A | 2/1993 | Nappholz et al. |
| 5,193,535 A | 3/1993 | Bardy et al. |
| 5,193,550 A | 3/1993 | Duffin |
| 5,197,467 A | 3/1993 | Steinhaus et al. |
| 5,207,219 A | 5/1993 | Adams et al. |
| 5,226,415 A | 7/1993 | Girodo et al. |
| 5,271,395 A | 12/1993 | Wahlstrand et al. |
| 5,282,836 A | 2/1994 | Kreyenhagen et al. |
| 5,284,491 A | 2/1994 | Sutton et al. |
| 5,292,338 A | 3/1994 | Bardy |
| 5,292,339 A | 3/1994 | Stephens et al. |
| 5,292,341 A | 3/1994 | Snell |
| 5,299,118 A | 3/1994 | Martens et al. |
| 5,311,874 A | 5/1994 | Baumann et al. |
| 5,312,448 A | 5/1994 | Hognelid et al. |
| 5,312,452 A | 5/1994 | Salo |
| 5,325,856 A | 7/1994 | Nitzsche et al. |
| 5,331,966 A | 7/1994 | Bennett et al. |
| 5,332,400 A | 7/1994 | Alferness |
| 5,334,220 A | 8/1994 | Sholder |
| 5,340,361 A | 8/1994 | Sholder |
| 5,341,811 A | 8/1994 | Cano |
| 5,350,406 A | 9/1994 | Nitzsche et al. |
| 5,350,409 A | 9/1994 | Stoop et al. |
| 5,356,425 A | 10/1994 | Bardy et al. |
| 5,360,437 A | 11/1994 | Thompson |
| 5,365,932 A | 11/1994 | Greenhut |
| 5,366,485 A | 11/1994 | Kroll et al. |
| 5,366,487 A | 11/1994 | Adams et al. |
| 5,372,607 A | 12/1994 | Stone et al. |
| 5,376,106 A | 12/1994 | Stahmann et al. |
| 5,379,776 A | 1/1995 | Murphy et al. |
| 5,383,910 A | 1/1995 | den Dulk |
| 5,387,229 A | 2/1995 | Poore |
| 5,391,189 A | 2/1995 | van Krieken et al. |
| 5,395,373 A | 3/1995 | Ayers |
| 5,395,397 A | 3/1995 | Lindgren et al. |
| 5,400,796 A | 3/1995 | Wecke |
| 5,411,524 A | 5/1995 | Rahul |
| 5,411,528 A | 5/1995 | Miller et al. |
| 5,411,531 A | 5/1995 | Hill et al. |
| 5,417,714 A | 5/1995 | Levine et al. |
| 5,423,869 A | 6/1995 | Poore et al. |
| 5,431,691 A | 7/1995 | Snell et al. |
| 5,433,198 A | 7/1995 | Desai |
| 5,437,285 A | 8/1995 | Verrier et al. |
| 5,462,060 A | 10/1995 | Jacobson et al. |
| 5,474,574 A | 12/1995 | Payne et al. |
| 5,480,413 A | 1/1996 | Greenhut et al. |
| 5,480,422 A | 1/1996 | Ben-Haim |
| 5,486,198 A | 1/1996 | Ayers et al. |
| 5,487,752 A | 1/1996 | Salo et al. |
| 5,487,755 A | 1/1996 | Snell et al. |
| 5,489,293 A | 2/1996 | Pless et al. |
| 5,507,782 A | 4/1996 | Kieval et al. |
| 5,507,784 A | 4/1996 | Hill et al. |
| 5,513,645 A | 5/1996 | Jacobson et al. |
| 5,514,163 A | 5/1996 | Markowitz et al. |
| 5,522,850 A | 6/1996 | Yomtov et al. |
| 5,522,859 A | 6/1996 | Stroebel et al. |
| 5,523,942 A | 6/1996 | Tyler et al. |
| 5,527,347 A | 6/1996 | Shelton et al. |
| 5,531,768 A | 7/1996 | Alferness |
| 5,534,016 A | 7/1996 | Boute |
| 5,540,232 A | 7/1996 | Laney et al. |
| 5,540,727 A | 7/1996 | Tockman et al. |
| 5,545,182 A | 8/1996 | Stotts et al. |
| 5,545,186 A | 8/1996 | Olson et al. |
| 5,549,649 A | 8/1996 | Florio et al. |
| 5,549,654 A | 8/1996 | Powell |
| 5,554,174 A | 9/1996 | Causey, III |
| 5,560,369 A | 10/1996 | McClure et al. |
| 5,560,370 A | 10/1996 | Verrier et al. |
| 5,562,711 A | 10/1996 | Yerich et al. |
| 5,584,864 A | 12/1996 | White |
| 5,584,867 A | 12/1996 | Limousin et al. |
| 5,591,215 A | 1/1997 | Greenhut et al. |
| 5,605,159 A | 2/1997 | Smith et al. |
| 5,607,460 A | 3/1997 | Kroll et al. |
| 5,613,495 A | 3/1997 | Mills et al. |
| 5,620,471 A | 4/1997 | Duncan |
| 5,620,472 A | 4/1997 | Rahbari |
| 5,620,473 A | 4/1997 | Poore |
| 5,622,178 A | 4/1997 | Gilham |
| 5,626,620 A | 5/1997 | Kieval et al. |
| 5,626,622 A | 5/1997 | Cooper |
| 5,626,623 A | 5/1997 | Kieval et al. |
| 5,632,267 A | 5/1997 | Hognelid et al. |
| 5,643,255 A | 7/1997 | Organ |
| 5,653,738 A | 8/1997 | Sholder |
| 5,674,250 A | 10/1997 | de Coriolis et al. |
| 5,674,251 A | 10/1997 | Combs et al. |
| 5,674,255 A | 10/1997 | Walmsley et al. |
| 5,676,153 A | 10/1997 | Smith et al. |
| 5,683,429 A | 11/1997 | Mehra |
| 5,683,431 A | 11/1997 | Wang |
| 5,690,686 A | 11/1997 | Min et al. |
| 5,690,689 A | 11/1997 | Sholder |
| 5,700,283 A | 12/1997 | Salo |
| 5,702,424 A | 12/1997 | Legay et al. |
| 5,713,928 A | 2/1998 | Bonnet et al. |
| 5,713,929 A | 2/1998 | Hess et al. |
| 5,713,930 A | 2/1998 | van der Veen et al. |
| 5,713,932 A | 2/1998 | Gillberg et al. |
| 5,716,382 A | 2/1998 | Snell |
| 5,716,383 A | 2/1998 | Kieval et al. |
| 5,716,384 A | 2/1998 | Snell |
| 5,718,235 A | 2/1998 | Golosarsky et al. |
| 5,724,985 A | 3/1998 | Snell et al. |
| 5,725,559 A | 3/1998 | Alt et al. |
| 5,725,561 A | 3/1998 | Stroebel et al. |
| 5,730,141 A | 3/1998 | Fain et al. |
| 5,730,142 A | 3/1998 | Sun et al. |
| 5,738,096 A | 4/1998 | Ben-Haim |
| 5,741,304 A | 4/1998 | Patwardhan et al. |
| 5,741,308 A | 4/1998 | Sholder |

| Patent | Date | Inventor |
|---|---|---|
| 5,749,901 A | 5/1998 | Bush et al. |
| 5,749,906 A | 5/1998 | Kieval et al. |
| 5,755,736 A | 5/1998 | Gillberg et al. |
| 5,755,737 A | 5/1998 | Prieve et al. |
| 5,755,739 A | 5/1998 | Sun et al. |
| 5,755,740 A | 5/1998 | Nappholz |
| 5,759,196 A | 6/1998 | Hess et al. |
| 5,772,604 A | 6/1998 | Langberg et al. |
| 5,776,164 A | 7/1998 | Ripart |
| 5,776,167 A | 7/1998 | Levine et al. |
| 5,782,887 A | 7/1998 | van Krieken et al. |
| 5,782,888 A | 7/1998 | Sun et al. |
| 5,788,717 A | 8/1998 | Mann et al. |
| 5,792,193 A | 8/1998 | Stoop |
| 5,792,200 A | 8/1998 | Brewer |
| 5,800,464 A | 9/1998 | Kieval |
| 5,800,471 A | 9/1998 | Baumann |
| 5,803,084 A | 9/1998 | Olson |
| 5,814,077 A | 9/1998 | Sholder et al. |
| 5,814,081 A | 9/1998 | Ayers et al. |
| 5,814,085 A | 9/1998 | Hill |
| 5,833,623 A | 11/1998 | Mann et al. |
| 5,836,975 A | 11/1998 | DeGroot |
| 5,836,987 A | 11/1998 | Baumann et al. |
| 5,840,079 A | 11/1998 | Warman et al. |
| 5,842,997 A | 12/1998 | Verrier et al. |
| 5,846,263 A | 12/1998 | Peterson et al. |
| 5,853,426 A | 12/1998 | Shieh |
| 5,855,593 A | 1/1999 | Olson et al. |
| 5,861,007 A | 1/1999 | Hess et al. |
| 5,865,838 A | 2/1999 | Obel et al. |
| 5,871,507 A | 2/1999 | Obel et al. |
| 5,873,895 A | 2/1999 | Sholder et al. |
| 5,873,897 A | 2/1999 | Armstrong et al. |
| 5,876,422 A | 3/1999 | van Groeningen |
| 5,891,170 A | 4/1999 | Nitzsche et al. |
| 5,891,178 A | 4/1999 | Mann et al. |
| 5,893,882 A | 4/1999 | Peterson et al. |
| 5,897,575 A | 4/1999 | Wickham |
| 5,902,324 A | 5/1999 | Thompson et al. |
| 5,916,239 A | 6/1999 | Geddes et al. |
| 5,928,271 A | 7/1999 | Hess et al. |
| 5,931,856 A | 8/1999 | Bouhour et al. |
| 5,931,857 A | 8/1999 | Prieve et al. |
| 5,935,081 A | 8/1999 | Kadhiresan |
| 5,944,744 A | 8/1999 | Paul et al. |
| 5,951,592 A | 9/1999 | Murphy |
| 5,961,467 A | 10/1999 | Shimazu et al. |
| 5,968,079 A | 10/1999 | Warman et al. |
| 5,968,081 A | 10/1999 | Levine |
| 5,974,341 A | 10/1999 | Er et al. |
| 5,978,707 A | 11/1999 | Krig et al. |
| 5,978,710 A | 11/1999 | Prutchi et al. |
| 5,983,138 A | 11/1999 | Kramer |
| 5,987,354 A | 11/1999 | Cooper et al. |
| 5,987,356 A | 11/1999 | DeGroot |
| 5,991,656 A | 11/1999 | Olson et al. |
| 5,991,657 A | 11/1999 | Kim |
| 5,991,662 A | 11/1999 | Kim et al. |
| 5,999,850 A | 12/1999 | Dawson et al. |
| 5,999,854 A | 12/1999 | Deno et al. |
| 6,014,581 A | 1/2000 | Whayne et al. |
| 6,017,307 A | 1/2000 | Raines |
| 6,026,320 A | 2/2000 | Carlson et al. |
| 6,041,251 A | 3/2000 | Kim et al. |
| 6,044,298 A | 3/2000 | Salo et al. |
| 6,047,210 A | 4/2000 | Kim et al. |
| 6,049,735 A | 4/2000 | Hartley et al. |
| 6,052,617 A | 4/2000 | Kim |
| 6,052,620 A | 4/2000 | Gillberg et al. |
| 6,058,328 A | 5/2000 | Levine et al. |
| 6,070,101 A | 5/2000 | Struble et al. |
| 6,081,745 A | 6/2000 | Mehra |
| 6,081,746 A | 6/2000 | Pendekanti et al. |
| 6,081,747 A | 6/2000 | Levine et al. |
| 6,081,748 A | 6/2000 | Struble et al. |
| RE36,765 E | 7/2000 | Mehra |
| 6,085,116 A | 7/2000 | Pendekanti et al. |
| 6,088,618 A | 7/2000 | Kerver |
| 6,091,988 A | 7/2000 | Warman et al. |
| 6,096,064 A | 8/2000 | Routh |
| 6,108,578 A | 8/2000 | Bardy et al. |
| 6,122,545 A | 9/2000 | Struble et al. |
| 6,128,529 A | 10/2000 | Esler |
| 6,128,533 A | 10/2000 | Florio et al. |
| 6,129,745 A | 10/2000 | Sun et al. |
| 6,134,469 A | 10/2000 | Wietholt |
| 6,151,524 A | 11/2000 | Krig et al. |
| 6,178,350 B1 | 1/2001 | Olson et al. |
| 6,219,579 B1 | 4/2001 | Bakels et al. |
| 6,223,072 B1 | 4/2001 | Mika et al. |
| 6,223,079 B1 | 4/2001 | Bakels et al. |
| 6,223,082 B1 | 4/2001 | Bakels et al. |
| 6,230,055 B1 | 5/2001 | Sun et al. |
| 6,238,420 B1 | 5/2001 | Bakels et al. |
| 6,240,317 B1 | 5/2001 | Villaseca et al. |
| 6,246,906 B1 | 6/2001 | Hsu et al. |
| 6,246,909 B1 | 6/2001 | Ekwall |
| 6,249,699 B1 | 6/2001 | Kim |
| 6,253,102 B1 | 6/2001 | Hsu et al. |
| 6,256,534 B1 | 7/2001 | Dahl |
| 6,263,242 B1 | 7/2001 | Mika et al. |
| 6,266,554 B1 | 7/2001 | Hsu et al. |
| 6,272,380 B1 | 8/2001 | Warman et al. |
| 6,275,734 B1 | 8/2001 | McClure et al. |
| 6,280,391 B1 | 8/2001 | Olson et al. |
| 6,285,907 B1 | 9/2001 | Kramer et al. |
| 6,289,248 B1 | 9/2001 | Conley et al. |
| 6,292,693 B1 | 9/2001 | Darvish et al. |
| 6,292,694 B1 | 9/2001 | Schloss et al. |
| 6,317,632 B1 | 11/2001 | Krig et al. |
| 6,321,117 B1 | 11/2001 | Koshiol et al. |
| 6,334,071 B1 | 12/2001 | Lu |
| 6,351,669 B1 | 2/2002 | Hartley et al. |
| 6,353,759 B1 | 3/2002 | Hartley et al. |
| 6,353,761 B1 | 3/2002 | Conley et al. |
| 6,400,981 B1 | 6/2002 | Govari |
| 6,408,209 B1 | 6/2002 | Bouhour et al. |
| 6,411,847 B1 | 6/2002 | Mower |
| 6,411,848 B2 | 6/2002 | Kramer et al. |
| 6,415,175 B1 | 7/2002 | Conley et al. |
| 6,421,564 B1 | 7/2002 | Yerich et al. |
| 6,424,865 B1 | 7/2002 | Ding |
| 6,430,438 B1 | 8/2002 | Chen et al. |
| 6,430,439 B1 | 8/2002 | Wentkowski et al. |
| 6,434,424 B1 | 8/2002 | Igel et al. |
| 6,438,410 B2 | 8/2002 | Hsu et al. |
| 6,438,421 B1 | 8/2002 | Stahmann et al. |
| 6,445,952 B1 | 9/2002 | Manrodt et al. |
| 6,484,058 B1 | 11/2002 | Williams et al. |
| 6,493,579 B1 | 12/2002 | Gilkerson et al. |
| 6,501,987 B1 | 12/2002 | Lovett et al. |
| 6,501,988 B2 | 12/2002 | Kramer et al. |
| 6,512,951 B1 | 1/2003 | Marcovecchio et al. |
| 6,522,925 B1 | 2/2003 | Gilkerson et al. |
| 6,526,317 B2 | 2/2003 | Hsu et al. |
| RE38,119 E | 5/2003 | Mower |
| 6,584,350 B2 | 6/2003 | Kim et al. |
| 6,658,286 B2 | 12/2003 | Seim |
| 6,671,548 B1 | 12/2003 | Mouchawar et al. |
| 6,687,541 B2 | 2/2004 | Marcovecchio et al. |
| 6,721,596 B1 | 4/2004 | Girouard et al. |
| 6,748,261 B1 | 6/2004 | Kroll et al. |
| 6,763,267 B2 | 7/2004 | Ding |
| 6,847,842 B1 | 1/2005 | Rodenhiser et al. |
| 6,957,100 B2 | 10/2005 | Vanderlinde et al. |
| 6,988,002 B2 | 1/2006 | Kramer et al. |
| 7,010,349 B2 | 3/2006 | Conley et al. |
| 7,039,461 B1 | 5/2006 | Lovett |
| 7,047,066 B2 | 5/2006 | Vanderlinde et al. |
| 7,062,325 B1 | 6/2006 | Krig et al. |
| 7,069,077 B2 | 6/2006 | Lovett et al. |
| 7,120,490 B2 | 10/2006 | Chen et al. |
| 7,142,915 B2 | 11/2006 | Kramer et al. |
| 7,142,918 B2 | 11/2006 | Stahmann et al. |
| 7,181,278 B2 | 2/2007 | Kramer et al. |
| 7,184,834 B1 | 2/2007 | Levine |
| 7,212,849 B2 | 5/2007 | Zhang et al. |

| | | |
|---|---|---|
| 7,212,860 B2 | 5/2007 | Stahmann et al. |
| 7,239,914 B2 | 7/2007 | Lovett et al. |
| 7,283,872 B2 | 10/2007 | Boute et al. |
| 7,349,734 B2 | 3/2008 | Stahmann et al. |
| 7,376,461 B2 | 5/2008 | Perschbacher et al. |
| 7,383,086 B2 | 6/2008 | Ding |
| 7,460,908 B2 | 12/2008 | Krig et al. |
| 7,532,931 B2 | 5/2009 | Gilkerson et al. |
| 7,606,620 B2 | 10/2009 | Gilkerson et al. |
| 7,680,530 B2 | 3/2010 | Vanderlinde et al. |
| 7,742,814 B2 | 6/2010 | Lovett |
| 7,805,192 B2 | 9/2010 | Stahmann et al. |
| 7,856,267 B2 | 12/2010 | Stahmann et al. |
| 2001/0014817 A1 | 8/2001 | Armstrong et al. |
| 2002/0062139 A1 | 5/2002 | Ding |
| 2002/0065539 A1 | 5/2002 | Von Arx et al. |
| 2002/0082509 A1 | 6/2002 | Vanderlinde et al. |
| 2002/0082660 A1 | 6/2002 | Stahmann et al. |
| 2002/0087198 A1 | 7/2002 | Kramer et al. |
| 2002/0091415 A1 | 7/2002 | Lovett et al. |
| 2002/0120298 A1 | 8/2002 | Kramer et al. |
| 2002/0147407 A1 | 10/2002 | Seim |
| 2002/0147471 A1 | 10/2002 | Seim |
| 2003/0004551 A1 | 1/2003 | Chen et al. |
| 2003/0069610 A1 | 4/2003 | Kramer et al. |
| 2003/0078630 A1 | 4/2003 | Lovett et al. |
| 2003/0105491 A1 | 6/2003 | Gilkerson et al. |
| 2003/0199928 A1 | 10/2003 | Hsu et al. |
| 2003/0233131 A1 | 12/2003 | Kramer et al. |
| 2004/0010295 A1 | 1/2004 | Kramer et al. |
| 2004/0015192 A1 | 1/2004 | Kim et al. |
| 2004/0077963 A1 | 4/2004 | Perschbacher et al. |
| 2004/0172076 A1 | 9/2004 | Stahmann et al. |
| 2004/0215245 A1 | 10/2004 | Stahmann et al. |
| 2004/0215249 A1 | 10/2004 | Corbucci |
| 2004/0215259 A1 | 10/2004 | Krig et al. |
| 2004/0243188 A1 | 12/2004 | Vanderlinde et al. |
| 2005/0038480 A1 | 2/2005 | Ding |
| 2005/0283196 A1 | 12/2005 | Bocek et al. |
| 2006/0095083 A1 | 5/2006 | Zhang et al. |
| 2006/0167520 A1 | 7/2006 | Gilkerson et al. |
| 2006/0195147 A1 | 8/2006 | Gilkerson et al. |
| 2006/0195150 A1 | 8/2006 | Lovett |
| 2006/0195151 A1 | 8/2006 | Vanderlinde et al. |
| 2007/0016258 A1 | 1/2007 | Krig et al. |
| 2007/0073348 A1 | 3/2007 | Stahmann et al. |
| 2007/0135853 A1 | 6/2007 | Kramer et al. |
| 2007/0142869 A1 | 6/2007 | Perschbacher et al. |
| 2007/0233201 A1 | 10/2007 | Lovett et al. |
| 2007/0288062 A1 | 12/2007 | Stahmann et al. |
| 2008/0167692 A1 | 7/2008 | Stahmann et al. |
| 2009/0076563 A1 | 3/2009 | Krig et al. |
| 2009/0149907 A1 | 6/2009 | Perschbacher et al. |
| 2010/0023075 A1 | 1/2010 | Gilkerson et al. |
| 2010/0145407 A1 | 6/2010 | Vanderlinde et al. |
| 2010/0222836 A1 | 9/2010 | Jarverud et al. |

FOREIGN PATENT DOCUMENTS

| | | |
|---|---|---|
| EP | 253505 A2 | 1/1988 |
| EP | 360412 A1 | 3/1990 |
| EP | 0360412 A1 | 3/1990 |
| EP | 0401962 A2 | 12/1990 |
| EP | 469817 A2 | 2/1992 |
| EP | 597459 A2 | 5/1994 |
| EP | 0597459 A2 | 5/1994 |
| EP | 0617980 A2 | 10/1994 |
| EP | 0744190 A2 | 11/1996 |
| EP | 0748638 A2 | 12/1996 |
| EP | 919256 A1 | 6/1999 |
| EP | 993842 A1 | 4/2000 |
| EP | 1112756 A2 | 7/2001 |
| JP | 07-072910 | 3/1995 |
| WO | WO-93/02746 A1 | 2/1993 |
| WO | WO-95/09029 A2 | 4/1995 |
| WO | WO-97/11745 A1 | 4/1997 |
| WO | WO-97/39798 A1 | 10/1997 |
| WO | WO-97/39799 A1 | 10/1997 |
| WO | WO-98/25669 A1 | 6/1998 |
| WO | WO-98/48891 A1 | 11/1998 |
| WO | WO-99/15232 A1 | 4/1999 |
| WO | WO-00/04950 A2 | 2/2000 |
| WO | WO-00/09206 A1 | 2/2000 |
| WO | WO-00/38782 A1 | 7/2000 |
| WO | WO-00/53089 A1 | 9/2000 |
| WO | WO-00/59573 A1 | 10/2000 |
| WO | WO-00/71200 A1 | 11/2000 |
| WO | WO-00/71202 A1 | 11/2000 |
| WO | WO-00/71203 A1 | 11/2000 |
| WO | WO-01/13993 A1 | 3/2001 |
| WO | WO-03/047690 A2 | 6/2003 |
| WO | WO-2006/049767 A1 | 5/2006 |

OTHER PUBLICATIONS

Metrix™ Model 3020 Implantable Atrial Defibrillator, Physician's Manual, InControl, Inc., Redmond, WA, (1998), pp. 4-24-4-27.

"U.S. Appl. No. 09/569,295, Non Final Office Action mailed Apr. 10, 2003", 11 pgs.

"U.S. Appl. No. 09/569,295, Non-Final Office Action mailed Oct. 23, 2002", 8 pgs.

"U.S. Appl. No. 09/569,295, Notice of Allowance mailed Jul. 5, 2005", 4 pgs.

"U.S. Appl. No. 09/569,295, Notice of Allowance mailed Aug. 25, 2005", 4 pgs.

"U.S. Appl. No. 09/569,295, Notice of Allowance mailed Nov. 29, 2005", 4 pgs.

"U.S. Appl. No. 09/569,295, Response filed Jan. 23, 2003 to Non-Final Office Action Mailed Oct. 23, 2002", 9 pgs.

"U.S. Appl. No. 09/569,295, Response filed Jul. 10, 2003 to Non-Final Office Action Mailed Apr. 10, 2003", 9 pgs.

"U.S. Appl. No. 09/569,295, Response filed Jul. 30, 2004 to Final Office Action Mailed Jul. 27, 2004", 10 pgs.

"U.S. Appl. No. 09/569,295, Advisory Action mailed Nov. 30, 2004", 2 pgs.

"U.S. Appl. No. 09/569,295, Final Office Action mailed Jan. 30, 2004", 6 pgs.

"U.S. Appl. No. 09/569,295, Final Office Action mailed Jul. 30, 2004", 7 pgs.

"U.S. Appl. No. 09/569,295, Notice of Allowance mailed Nov. 17, 2005", 2 pgs.

"U.S. Appl. No. 09/569,295, Response filed Apr. 22, 2005 to Restriction Requirement mailed Mar. 23, 2005", 6 pgs.

"U.S. Appl. No. 09/569,295, Response filed Nov. 6, 2003 to Restriction Requirement mailed Oct. 6, 2003", 8 pgs.

"U.S. Appl. No. 09/569,295, Restriction Requirement mailed Mar. 23, 2005", 4 pgs.

"U.S. Appl. No. 09/569,295, Restriction Requirement mailed Oct. 6, 2003", 4 pgs.

"U.S. Appl. No. 09/579,951, Amendment Under 37 CFR 1.312 filed Oct. 10, 2002", 2 pgs.

"U.S. Appl. No. 09/579,951, Final Office Action mailed Dec. 14, 2001", 8 pgs.

"U.S. Appl. No. 09/579,951, Non Final Office Action mailed Jul. 6, 2001", 7 pgs.

"U.S. Appl. No. 09/579,951, Notice of Allowance mailed Jul. 10, 2002", 5 pgs.

"U.S. Appl. No. 09/579,951, Response filed May 10, 2002 to Final Office Action mailed Dec. 14, 2001", 5 pgs.

"U.S. Appl. No. 09/579,951, Response filed Oct. 5, 2001 to Non-Final Office Action mailed Jul. 6, 2001", 16 pgs.

"U.S. Appl. No. 09/748,358, Notice of Allowance mailed Jun. 26, 2002", 6 pgs.

"U.S. Appl. No. 10/017,800, Advisory Action mailed Apr. 21, 2005", 3 pgs.

"U.S. Appl. No. 10/017,800, Advisory Action mailed Apr. 27, 2006", 3 pgs.

"U.S. Appl. No. 10/017,800, Response filed Apr. 24, 2006 to Final Office Action mailed Feb. 24, 2006", 13 pgs.

"U.S. Appl. No. 10/017,800, Amendment and Response filed Sep. 6, 2005 to Non-Final Office Action mailed Jul. 5, 2005", 14 pgs.

"U.S. Appl. No. 10/017,800, Appeal Brief filed Jul. 10, 2006", 23 pgs.

"U.S. Appl. No. 10/017,800, Final Office Action mailed Feb. 8, 2005", 8 pgs.

"U.S. Appl. No. 10/017,800, Final Office Action mailed Feb. 24, 2006", 8 pgs.
"U.S. Appl. No. 10/017,800, Final Office Action mailed Nov. 15, 2005", 8 pgs.
"U.S. Appl. No. 10/017,800, Non-Final Office Action mailed Jul. 5, 2005", 10 pgs.
"U.S. Appl. No. 10/017,800, Non-Final Office Action mailed Aug. 24, 2004", 6 pgs.
"U.S. Appl. No. 10/017,800, Notice mailed Jul. 25, 2006", 3 pgs.
"U.S. Appl. No. 10/017,800, Notice of Allowance mailed Feb. 20, 2007", 6 pgs.
"U.S. Appl. No. 10/017,800, Notice of Allowance mailed Oct. 27, 2006", 6 pgs.
"U.S. Appl. No. 10/017,800, Preliminary Amendment filed Jan. 12, 2007", 4 pgs.
"U.S. Appl. No. 10/017,800, Response filed Jan. 13, 2006 to Final Ofice Ation mailed Nov. 15, 2005", 14 pgs.
"U.S. Appl. No. 10/017,800, Response filed Apr. 5, 2005 to Final Office Action mailed Feb. 8, 2005", 14 pgs.
"U.S. Appl. No. 10/017,800, Response filed Aug. 2, 2006 to Notice of Non-Compliant Appeal Brief mailed Jul. 25, 2006", 21 pgs.
"U.S. Appl. No. 10/017,800, Response filed Nov. 23, 2004 to Non-Final Office Action mailed Aug. 24, 2004", 15 pgs.
"U.S. Appl. No. 10/107,800, Supplemental Amendment & Response filed May 9, 2005 to Advisory Action mailed Apr. 21, 2005 and Final Office Action mailed Feb. 8, 2005", 14 pgs.
"U.S. Appl. No. 10/304,149, Notice of Allowance mailed Jul. 19, 2005", 7 pgs.
"U.S. Appl. No. 10/304,149, Non-Final Office Action mailed Mar. 3, 2004", 7 pgs.
"U.S. Appl. No. 10/304,149, Response filed Jul. 6, 2004 to Non-Final Office Action mailed Mar. 3, 2004", 6 pgs.
"U.S. Appl. No. 10/304,149, Preliminary Amendment filed Mar. 21, 2003", 3 pgs.
"U.S. Appl. No. 10/306,514, Non-Final Office Action mailed Mar. 24, 2005", 7 pgs.
"U.S. Appl. No. 10/306,514, Notice of Allowance mailed Sep. 15, 2005", 4 pgs.
"U.S. Appl. No. 10/306,514, Response filed Jul. 25, 2005 to Non-Final Office Action mailed Mar. 24, 2005", 6 pgs.
"U.S. Appl. No. 11/380,148, Final Office Action mailed Nov. 10, 2009", 5 pgs.
"U.S. Appl. No. 11/380,148, Response filed Dec. 1, 2008 to Restriction Requirement mailed Oct. 29, 2008", 6 pgs.
"U.S. Appl. No. 11/380,148, Restriction Requirement mailed Oct. 29, 2008", 7 pgs.
"U.S. Appl. No. 11/380,148, Examiner Interview Summary mailed Apr. 3, 2009", 1 pg.
"U.S. Appl. No. 11/380,148, Non Final Office Action mailed Apr. 3, 2009", 8 pgs.
"U.S. Appl. No. 11/380,148, Notice of Allowance mailed Feb. 22, 2010", 5 pgs.
"U.S. Appl. No. 11/380,148, Response filed Jan. 11, 2010 to Final Office Action mailed Nov. 10, 2009", 5 pgs.
"U.S. Appl. No. 11/380,148, Response filed Jul. 6, 2009 to Non Final Office Action mailed Apr. 3, 2009", 8 pgs.
"U.S. Appl. No. 11/380,148, Restriction Requirement mailed Mar. 6, 2009", 8 pgs.
"French CNH Equipment Approvals", *Clinica*, 417, p. 9, (Sep. 5, 1990), 3 pgs.
"Harmony™, Automatic Dual Chamber Pacemaker, Product Information and Programming Guide", Viatron Medical, 22 p., (Published Prior to Nov. 13, 2003), Harmony Dual Chamber mentioned in publication *Clinica*, 467, p. 16, Sep. 11, 1991, "Rate Devices Impact Pacemaker Market", also mentioned in *Clinica*, 417, p. 9, Sep. 5, 1990 French CNH Equi, 22 pgs.
"Pacemaker System Guide for PULSAR MAX II; Mulitprogrammable Pacemakers", Product brochure published by Guidant Corporation, (Apr. 18, 1999), pp. 6-48 and 6-49.
"Pacemaker System Guide for PULSAR MAX II; Multiprogrammable Pacemakers", Product brochure published by Guidant Corporation, (Apr. 18, 1999), pp. 6-39-6-51.

"Rate-Adaptive Devices Impact Pacemaker Market", *Clinica*, 467, p. 16, (Sep. 11, 1991), 6 pgs.
"Vitatron Medical Harmony Automatic Dual Chamber Pacemaker Product Information and Programming Guide", Viatron Medical, 22 p., (Date Unknown), Harmony Dual Chamber mentioned in publication Clinica, 467, p. 16, Sep. 11, 1991, "Rate Devices Impact Pacemaker Market", also mentioned in Clinica, 417, p. 9, Sep. 5, 1990 "French CNH Equipment Approvals"., Product Brochure published by Vitatron Medical, 22 pgs.
Ayers, G. M., et al., "Ventricular Proarrhythmic Effects of Ventricular Cycle Length and Shock Strength in a Sheep Model of Transvenous Atrial Defibrillation", *Circulation*, 89 (1), (Jan. 1994), 413-422.
Blommaert, D., et al., "Effective Prevention of Atrial Fibrillation by Continuous Atrial Overdrive Pacing After Coronary Artery Bypass Surgery", *JACC*, vol. 35, No. 6, (May 2000), 1411-1415.
Buhr, T. A, et al., "Novel Pacemaker Algorithm Diminishes Short-Coupled Ventricular Beats in Atrial Fibrillation", *Pacing and Clinical Electrophysiology*, 24(Part II), (Apr. 2001), 729.
Campbell, R. M., et al., "Atrial Overdrive Pacing for Conversion of Atrial Flutter in Children", *Pediatrics*, 75(4), (Apr. 1985), 730-736.
Clark, D. M., et al., "Hemodynamic Effects of an Irregular Sequence of Ventricular Cycle Lengths During Atrial Fibrillation", *JACC*, vol. 30, No. 4, (Oct. 1997), 1039-1045.
Duckers, H. J., et al., "Effective use of a novel rate-smoothing algorithm in atrial fibrillation by ventricular pacing", *European Heart Journal*, 18, (1997), pp. 1951-1955.
Fahy, G. J., et al., "Pacing Strategies to Prevent Atrial Fibrillation", *Atrial Fibrillation*, 14 (4), (Nov. 1996), 591-596.
Fromer, M., et al., "Algorithm for the Prevention of Ventricular Tachycardia Onset: The Prevent Study", *The American Journal of Cardiology*, 83 (5B), (Mar. 11, 1999),. pp. 45D-47D.
Garrigue, S., et al., "Prevention of Atrial Arrhythmias during DDD Pacing by Atrial Overdrive", *Pacing and Clinical Electrophysiology*, 21, , (Sep. 1998), 1751-1759.
Greenhut, S., et al., "Effectiveness of a Ventricular Rate Stabilization Algorithm During Atrial Fibrillation in Dogs", *Pace Abstract*, Abstract No. 60, (1996), 1 pg.
Guidant, "CONTAK TR™ CHFD™ Model 1241", System Guide, Congestive Heart Failure Device, (1999), 1-191.
Heuer, H., et al., "Dynamic Dual-Chamber Overdrive Pacing with an Implantable Pacemaker System: A New Method for Terminating Slow Ventricular Tachycardia", Zeitschrift fur Kardiologie, 75, German Translation by the Ralph McElroy Translation Company, Austin, TX, (1986), 6 pgs.
Heuer, H., et al., "Dynamische Zweikammer-Overdrive-Stimulation mit einem implantierbaren Schrittmachersystem als neue Methode zur Beendigung Langsamer ventrikularer Tachykardien", *Z Kardiol*, 75, Includes English translation (5 pgs.), (1986), 673-675.
Jenkins, "Diagnosis of Atrial Fibrillation Using Electrogram from Chronic Leads: Evaluation of Computer Algorithm", *Pacing and Clinical Electrophysiology*, 11(5), (1988), 622-631.
Jung, J., et al., "Discrimination of Sinus Rhythm, Atrial Flutter, and Atrial Fibrillation Using Bipolar Endocardial Signals", *Journal of Cardiovascular Electrophysiology*, 9(7), (Jul. 1998), 689-695.
Krig, D. B., "Method and Apparatus for Treating Irregular Ventricular Contractions Such As During Atrial Arrhythmia", U.S. Appl. No. 10/643,590, filed Aug. 19, 2003, 45 pgs.
Lau, Chu-Pak, et al., "Efficacy of Ventricular Rate Stabilization by Right Ventricular Pacing During Atrial Fibrillation", *Pacing and Clinical Electrophysiology*, 21(3), (1998), 542-548.
Medtronic, "INSYNC® III Device Model 8042", Device Programming Guide, INSYNC III Device Model 8042, Vision Programmer Software Model 9981, (2000), 1-260.
Medtronic, "INSYNC® III Device Model 8042", Device Reference Guide, INSYNC III Device Model 8042, Vision Programmer Software Model 9981, (2002), 1-252.
Mehra, R., et al., "Chapter 34—Prevention of Atrial Fibrillation/Flutter by Pacing Techniques", *Interventional Electrophysiology*, Second Edition, Futura Publishing.Company, Inc., (1996), pp. 521-540.
Morris, M. M., et al., "Intracardiac Electrogram Transformation: Morphometric Implications for Implantable Devices", *Journal of Electrocardiology*, 29 Supplement, (1996), 124-129.

Mower, Morton, U.S. Appl. No. 10/214,474, filed Aug. 8, 2002, entitled "Method and Apparatus for Treating Hemodynamic Disfunction".

Murgatroyd, F. D., et al., "A New Pacing Algorithm for Overdrive Suppression of Atrial Fibrillation", *Pacing and Clinical Electrophysiology*, 17(11), (1994),1966-1973.

Schuller, H., et al., "Far Field R-Wave Sensing—An Old Problem Repeating", (NASPE Abstract 264), *Pacing and Clinical Electrophysiology*, 19( Part II), (1996), p. 631.

Seim, G., et al., "Classification of Atrial Flutter and Atrial Fibrillation Using an Atrial Dispersion Index (ADI)", Guidant CRM Therapy Research Peer Review Report Revision 2.0, (Jan. 6, 1999), 27 pgs.

St. Jude Medical, "Atlas™ + HF Models V-343, V-341", User's Manual, Implantable Cardioverter-Defibrillator, (Sep. 2003), 1-30.

St. Jude Medical, "Epic™ HF Model V-339", User's Manual, Implantable Cardioverter-Defibrillator, (Jul. 2002), 1-26.

St. Jude Medical, "Model 3510 Programmer with Model 3307 Software", Reference Manual, for Atlas™, Atlas™ +, Epic™, Epic™ +, Photon u and Photon Implantable Cardioverter/Defibrillators, (Sep. 2003), 1-314.

Stephany, G. R., et al., "Real-Time Estimation of Magnitude-Square Coherence for Use in Implantable Devices", *IEEE Computers in Cardiology*, (1992), 375-378.

Sutton, R., "Pacing in Atrial Arrhythmias", *Pacing and Clinical Electrophysiology*, 13(12 Pt. 2), (1990), 1823-1827.

Swiryn, S., et al., "Chapter 21—Detection of Atrial Fibrillation by Pacemakers and Antiarrhythmic Devices", *Nonpharmacological Management of Atrial Fibrillation*, Futura Publishing Co, Inc. Armonk, NY, (1997), 309-318.

Wittkampf, F.H.M., et al., "Rate Stabilization by Right Ventricular Pacing in Patients with Atrial Fibrillation", *Pacing and Clinical Electrophysiology*, 9(6)(Part 2), (Nov.-Dec. 1986), 1147-1153.

Wittkampf, F. H.M., et al., "Effect of Right Ventricular Pacing on Ventricular Rhythm During Atrial Fibrillation", *J. Am. Coll. Cardiol.*,11(3), (Mar. 1988), 539-545.

Zhu, D. W, "Electrophysiology, Pacing and Arrhythmia—Pacing Therapy for Atrial Tachyarrhythmias", *Clinical Cardiology*, 19(9), (1996), 737-742.

"U.S. Appl. No. 11/759,354, Non Final Office Action mailed Dec. 10, 2010", 11 pgs.

"Screenshots taken of Display of Model 2920 Programmer, Using Model 2845 Software Application", Guidant Corporation, Effective Date of First Use: Dec. 2, 1999., 5 pgs.

Alonso, C., "Electrocardiographic Predictive Factors of Long-Term Clinical Improvement with Multisite Biventricular Pacing in Advanced Heart Failure", *The American Journal of Cardiology (US)*, vol. 84, No. 12, (Dec. 1999), 1417-1421.

Cohen, R. J., et al., "Quantitative Model for Ventricular Response During Atrial Fibrillation", *IEEE Transactions on Biomedical Engineering*, 30, (1983), 769-782.

Das, G., "QT interval and repolarization time in patients with intraventricular conduction delay", *J. Electrocardiol.*, 23(1), (Jan. 1990), 49-52.

Guidant, "CONTAK CD® CRT-D 1823", *Physician's System Manual, Cardiac Resynchronization Therapy Defibrillator*, (2002), 193 pgs.

Guidant, "CONTAK® Renewal™ Model H135", *System Guide*, (2003), 1-331.

Hsia, Peng W., et al., "Improved Nonthoracotmy Defibrillation Based on Ventricular Fibrillation Waveform Characteristics", *PACE, 18—NASPE Abstracts*, (Abstract No. 29), (Apr. 1995), p. 803.

Hsu, William, et al., "Effect of Shock Timing on Defibrillation Success" *Pacing Clin Electrophysiol.*, 20(1 Pt 2), (Jan. 1997), 153-157.

Lau, C. P., et al., "A new pacing method for rapid regularization and rate control in atrial fibrillation", *Am J Cardiol.*, 65 (18), (May 15, 1990), 1198-203.

Medtronic, "INSYNC® Device Model 8040", Device Reference Guide, (Aug. 2001), 1-276.

Medtronic, "INSYNC® ICD 7272", System Reference Guide, Dual chamber implantable cardioverter defibrillator with cardiac resynchronization therapy. A guide to the operation and programming of the 7272 InSync® ICD Dual Chamber ImpLantable Cardioverter Defibrillator, (Jun. 2002), 1-367.

Medtronic, "INSYNC Marquis™ 7277", Reference Manual, Dual Chamber Implantable Cardioverter Defibrillator, (Mar. 2003), 1-435.

Medtronic, "INSYNC® Model 8040 Device Programming Guide", Device Programming Guide, Device Model 8040 & Programmer Software Model 9980, (2001), 1-204.

Medtronic, "Marquis™ DR 7274 Dual Chamber Implantable Cardioverter Defibrillator", *Reference Manual*, (Feb. 2002), 426 pgs.

Prinzen, F. W., et al., "Optimization of ventricular function by improving the activation sequence during ventricular pacing", *Pacing Clin Electrophysiol.*, 21(11 Pt 2), (Nov. 1998), 2256-60.

Saxon, L. A., et al., "Acute effects of intraoperative multisite ventricular pacing on left ventricular function and activation/contraction sequence in patients with depressed ventricular function.", *J Cardiovasc Electrophysiol.*, 9(1), (Jan. 1998), 13-21.

Sweeney, M. O., et al., "Adverse Effect of Ventricular Pacing on Heart Failure and Atrial Fibrillation Among Patients With Normal Baseline QRS Duration in a Clinical Trial of Pacemaker Therapy for Sinus Node Dysfunction", *Circulation*, 107(23), (Jun. 17, 2003), 2932-2937.

Tse, H. F., et al., "Effects of ventricular rate regularization pacing on quality of life and symptoms in patients with atrial fibrillation (Atrial fibrillation symptoms mediated by pacing to mean rates [AF Symptoms study])", *Am J Cardiol.*, 94(7), (Oct. 2004), 938-941.

Zhu, D., et al., "Pacing therapy for atrial tachyarrhythmias", *Clin. Cardiol.*, 19(9), (Sep. 1996), 737-742.

"U.S. Appl. No. 11/759,394, Response filed Jul. 26, 2011 to Final Office Action mailed Apr. 28, 2011", 9 pgs.

CARDIAC PACING SYSTEM FOR PREVENTION OF VENTRICULAR FIBRILLATION AND VENTRICULAR TACHYCARDIA EPISODE

CROSS-REFERENCE TO RELATED APPLICATIONS

This application is a divisional of U.S. application Ser. No. 11/380,148, filed on Apr. 25, 2006, now issued as U.S. Pat. No. 7,742,814 which is a divisional of U.S. application Ser. No. 09/569,295, filed on May 13, 2000, now U.S. Pat. No. 7,039,461, the specifications of which are incorporated herein by reference.

FIELD OF THE INVENTION

The present invention relates generally to cardiac devices and in particular to a cardiac pacing system for prevention of ventricular fibrillation and ventricular tachycardia episodes.

BACKGROUND

Implantable cardiac pacemakers have been in existence since the latter portion of the 1950s. Continuing advances in lead and pulse generator design have evolved, resulting in a variety of pacing modes and pacing parameters for both single chamber and multiple chamber pacing devices.

Researchers continue to study the electromechanical nature of the heart in search of better ways to diagnose and treat cardiac arrhythmia. For example, researchers intent on understanding the operation of the heart watch for repeatable electrical patterns indicating specific cardiac arrhythmia. If identified, such electrical patterns are useful as a diagnostic tool to determine when specific arrhythmia are about to occur (or are more likely to occur). Electronics in the implantable device may be used to identify such electrical patterns and provide appropriate therapy.

One electrical pattern observed at the onset of ventricular tachyarrhythmia and/or ventricular fibrillation in some cases is the so-called "short-long-short" induction pattern. FIG. 1 illustrates the short-long-short induction sequence. In this example, the first premature ventricular contraction (PVC-1 in FIG. 1) causes the first short interval and the long interval. In this example, the second short interval is caused by a second premature ventricular contraction (PVC-2 in FIG. 1). However, the short-long-short pattern is not observed prior to each episode of ventricular tachyarrhythmia and/or ventricular fibrillation. The short-long-short pattern results in extreme variations in instantaneous ventricular rate.

One attempt at limiting rate variation was offered in U.S. Pat. No. 4,562,841, to Brockway et al., issued Jan. 7, 1986. One device discussed in the '841 patent included a rate smoothing function for preventing the rate interval from changing by more than a predetermined percentage on a cycle-to-cycle basis; and a graceful degradation function for causing the ventricular pacing rate to each day when the atrial rate exceeds a programmed upper rate limit for a predetermined length of time. Among other later works, the Prevent study investigated whether a rate smoothing algorithm decreases the onset of ventricular tachyarrhythmia. *The American Journal of Cardiology*, vol. 83 (5B), Mar. 11, 1999, pp. 45D-47D. One goal of this rate smoothing algorithm was to prevent abrupt changes in heart rate by pacing and to increase or decrease the pace rate gradually. The rate smoothing algorithm allowed increases or decreases in pacing rate only within a given percentage of the last V-V interval.

However, one limitation of the rate smoothing algorithm is that the rate smoothing algorithm is always executing so the pacing pulses are delivered at a pacing rate which cannot vary outside the given percentage of the last V-V interval. Thus, the rate smoothed device may underpace when cardiac rate would normally increase rapidly and may overpace when cardiac rate would normally decrease rapidly. Additionally, the rate smoothing algorithm views the pacing interval only in the context of the last V-V interval, which is a limited representation of the patient's heart rate. The proposed systems are limited to rate analysis and do not include other sources of information about the patient's condition.

What is needed in the art is a cardiac pacing system for reducing ventricular tachyarrhythmia and ventricular fibrillation which adapts to cardiac demands and which does not does not constrain pacing rate changes to a given percentage of a last V-V interval. The cardiac pacing system should have an accurate representation of a patient's heart rate and should incorporate any other information which may assist in identifying possible ventricular tachyarrhythmia and ventricular fibrillation.

SUMMARY

The present cardiac pacing system solves the foregoing problems and others not expressly stated herein. One aspect of the present pacing system is the reduction of long pauses between pacing events by tracking an elapsed time since the last ventricular event and sending an instruction to a pacing device to interrupt the long pause if the intervening event is not observed within an event window. Such long pause prevention has uses in both atrial and ventricular pacing applications. In ventricular pacing applications it prevents the short-long-short induction sequence by introducing a ventricular contraction to break up the "long" period. In atrial pacing applications it serves to regularize atrial pacing to avoid atrial arrhythmia.

Another aspect of the present pacing system is that the event window is calculated using a plurality of intervals, in one embodiment, to obtain a better rate estimation and a more complete context for rate calculations.

Another aspect of the present pacing system is that the event window is dynamically adjusted to adapt for variations in heart rate. For example, embodiments will be described which use rate trajectory, which is the first derivative of heart rate, to shorten the event window when pacing rate is increasing and to lengthen the event window when pacing rate is decreasing.

Another aspect of the present pacing system is that information other than rate information may be used to determine the sensitivity of the system and parameter values. For example, in one embodiment, the sensitivity of the system is increased during certain times based on morphological information and/or other sensor information indicating possible ventricular tachyarrhythmia and/or ventricular fibrillation onset.

Another aspect of the present pacing system is that it may be used in both single mode and dual mode pacing applications and devices and with atrial and/or ventricular arrhythmia applications.

This summary is intended to provide an overview of the subject matter of the present patent application. It is not intended to provide an exhaustive or exclusive explanation of the invention. The detailed description is included to provide further information about the subject matter of the present patent application.

DETAILED DESCRIPTION

This detailed description provides details on how to make in use the present invention, including a best mode of the invention. The embodiments provided herein may differ in electrical, mechanical, and chemical nature without departing from the scope of the present invention. It is understood that some organizational variation in the embodiments of apparatus and order of method provided herein may exist which fall within the scope of the present invention, which is provided by the appended claims and equivalents thereto.

Although initial embodiments described herein will relate to ventricular pacing therapy it is understood that subsequent embodiments relating to atrial pacing therapy are also described. The embodiments will also include single chamber and dual chamber applications. It is understood that the apparatus and method provided herein is not limited to implantable devices, and may be used in devices external to the body. Additionally, other devices may employ the aspects presented herein without departing from the scope of the present invention.

For the purposes of this document, a ventricular contraction or atrial contraction refers to an actual ventricular or actual atrial contraction, respectively. A ventricular contraction event refers to an electronic, acoustic, or other type of signal associated with the actual ventricular contraction. An atrial contraction event refers to an electronic, acoustic, or other type of signal associated with the actual atrial contraction. This distinction is made to recognize that pacing devices use signals representing the actual activity of the heart. It is understood that these signals (events) may incur delays and other defects, depending on the type of signal being monitored, with respect to the actual activity in the heart.

One aspect of the present pacing system is the reduction of long pauses between cardiac events by tracking an elapsed time since the last event and sending an instruction to a pacing device to initiate an event if no such event is observed within an event window. Such long pause prevention avoids the short-long-short induction sequence by introducing a contraction to break up the "long" period. This aspect is applicable in treatment of both ventricular and atrial arrhythmia, since the event window approach may be used to break up a "long" period between ventricular/atrial pulses and regularize the pacing.

Figure 5:
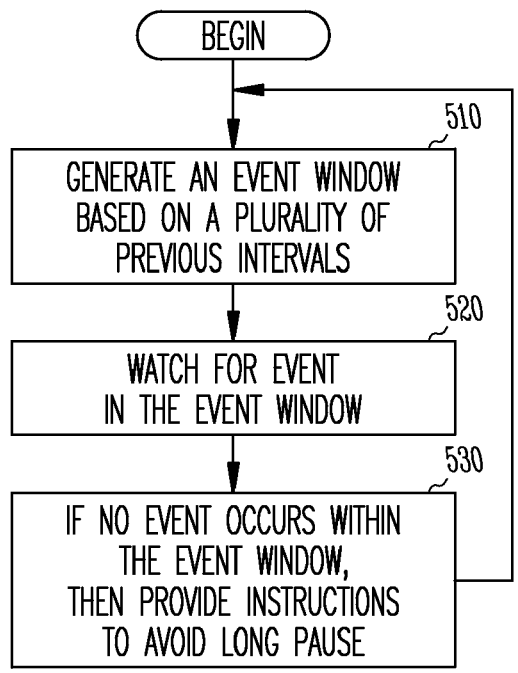
FIG. 5 is a flowchart demonstrating the use of the event window, according to one embodiment of the present system.

Another aspect of the present pacing system is that the event window is calculated using a plurality of intervals, in one embodiment, to obtain a better instantaneous rate estimation. FIG. 5 shows one embodiment where a plurality of previous intervals are used to generate the event window (510). The system watches for an event to occur within the event window (520), such as a ventricular contraction event in the ventricular pacing application. If no event occurs within the event window, then an instruction is issued to prevent a long pause (530). In the ventricular pacing application this may be a ventricular contraction caused by directly pacing a ventricle or via an atrial pace and the subsequent contraction of the ventricle. One way to express an event window generated from a plurality of intervals is:

$$\text{event window} = \text{function(plurality of intervals)}.$$

Figure 1:
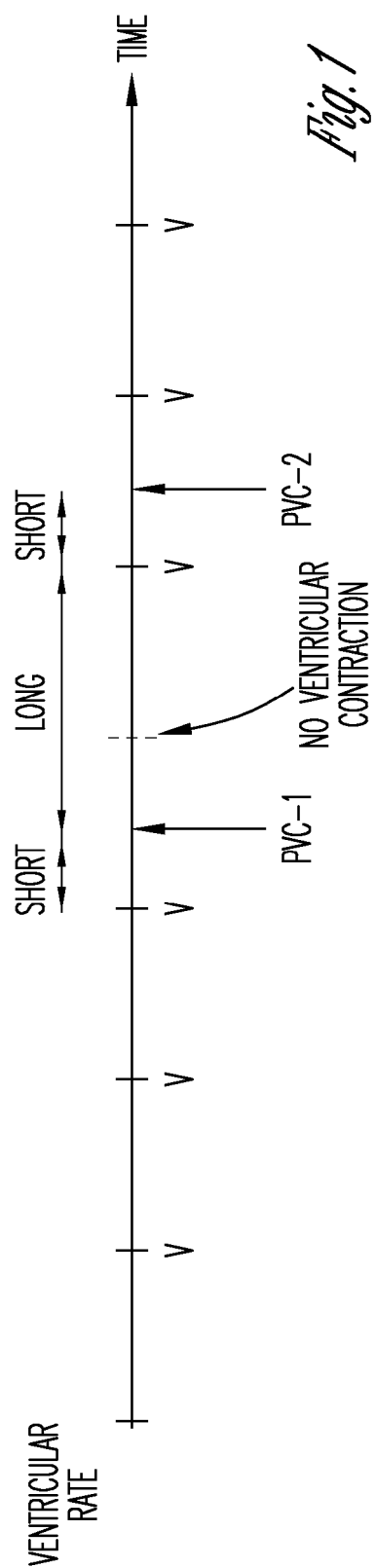
FIG. 1 is a timing diagram showing a number of ventricular contraction events and a short-long-short induction sequence, which is observed before some episodes of ventricular tachyarrhythmia and/or ventricular fibrillation.
Figure 2:
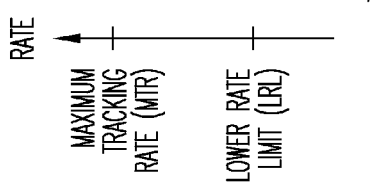
FIG. 2 is a pacing rate chart showing a lower rate limit and a maximum tracking rate.
Figure 3:
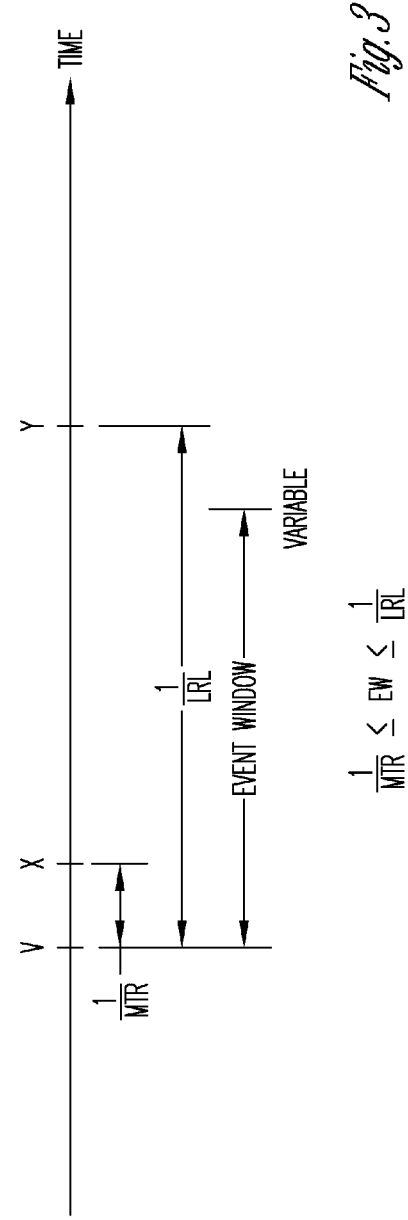
FIG. 3 is a timing diagram showing a last ventricular contraction event V, and an event window bounded by the 1/(MTR) and 1/(LRL) boundaries, according to one embodiment of the present system.

One skilled in the art will readily recognize that several functions may be used without departing from the scope of the present invention. Unlike the rate smoothing approach, which relies on the last V-V interval and is limited to a fixed percentage of the last V-V interval, the present event window, in one embodiment, is generated using a plurality of previous intervals to provide a better context for determination of instantaneous rate. FIG. 3 illustrates an event window according to one embodiment of the present system. In this embodiment, the event window has a duration which may range between the inverse of the maximum tracking rate (1/MTR) and the inverse of the lower rate limit (1/LRL), for ventricular applications. (Analogous limitations may be applied in the case of atrial pacing.) If the event window was allowed to have a duration less than 1/MTR, then a subsequent initiated pace may result in a rate greater than the maximum tracking rate, which is undesirable. Additionally, if the event window was allowed to have a duration in excess of 1/LRL, then a subsequent initiated pace would result in a rate less than the lower rate limit of the device, which is also undesirable. However, since another aspect of the present pacing system is that the event window is dynamically adjusted to adapt for variations in heart rate, the duration of the event window may vary between these limits in this embodiment.

In one embodiment, the event window is calculated by averaging a number, N, of previous intervals to obtain an approximation of the current pacing rate. In one embodiment, N is any integer greater than 1. In one embodiment, N is equal to 2. In one embodiment, N is equal to 5. In one embodiment, N is equal to 10. In one embodiment, N varies depending on average rate. In one embodiment, N varies depending on standard deviation of a predetermined number of interval samples. The examples and ranges for determination of N are provided herein to demonstrate the flexibility of the present system and are not intended in exclusive or exhaustive sense. It is understood that other values for N and systems for determination of N may be used without departing from the scope of the present pacing system.

In one embodiment, the event window is calculated by a weighted average of N intervals, where N is greater than 1. For example, in one embodiment, the more recent intervals are weighted stronger than less recent intervals to give a weighting effect to the latest trend in interval length. In one embodiment, the event window is calculated by interpolation from previous intervals. In one embodiment, the event window is produced from a linear regression of N intervals, where N is an integer greater than 1. Other curve fitting approaches may be used without departing from the present pacing system. It is understood that other functions of the previous intervals may be employed without departing from the scope of the present pacing system.

Figure 4A:
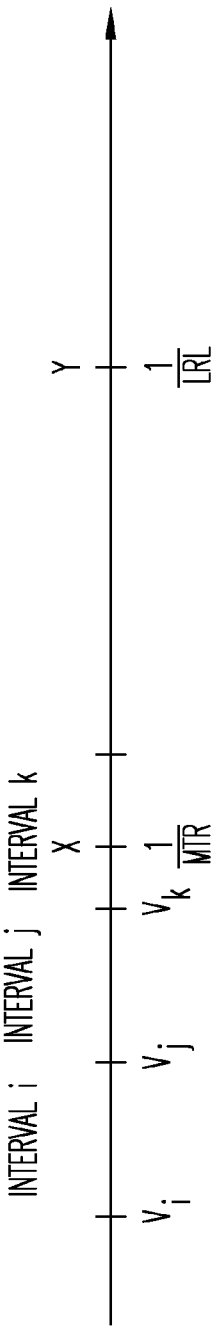
FIG. 4A is a timing diagram showing a plurality of ventricular contraction events separated by intervals and the 1/(MTR) and 1/(LRL) boundaries for the event windows shown in FIGS. 4B, 4C and 4D, according to one embodiment of the present system.
Figure 4B:
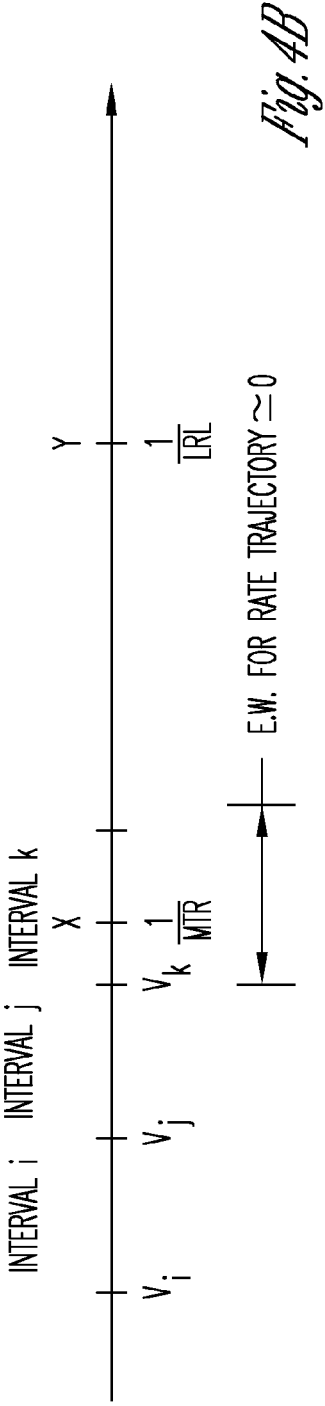
FIG. 4B demonstrates an event window (E.W.) for rate trajectory approximately equal to zero, according to one embodiment of the present system.
Figure 6:
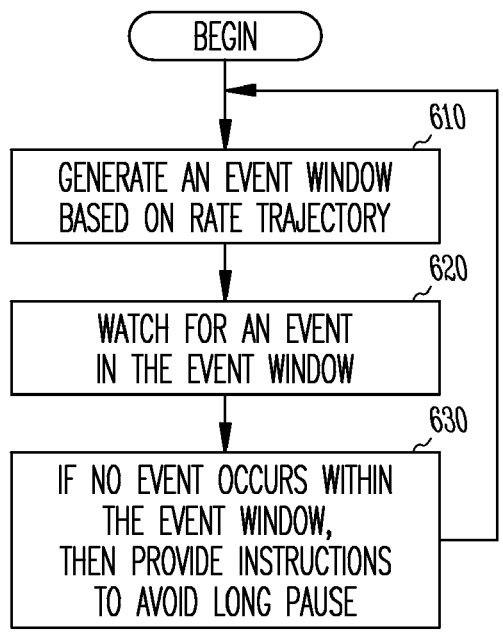
FIG. 6 is a flowchart demonstrating the use of the event window, according to one embodiment of the present system.

FIG. 6 shows one embodiment where the event window is calculated using rate trajectory to dynamically adjust event window size (610). The system then watches for an event during the event window (620) and issues an instruction to avoid a long pause if no event is detected within the window (630). Rate trajectory is the first time derivative of rate. For example, in one embodiment shown in FIG. 4A-4D (for ventricular pacing) the event window is shortened for positive rate trajectory and lengthened for negative rate trajectory. In this example, if Vk is the last ventricular contraction event, then the interval k can be estimated using previous interval i and interval j (and perhaps other intervals and factors), and the event window is dynamically adjusted as follows:

1. Rate trajectory approximately 0: if rate trajectory is approximately zero, then the interval i is approximately the same duration as interval j and the event window is a bit longer than the estimated interval k to allow the heart to intrinsically pace the ventricle, as shown in FIG. 4B.

2. Rate trajectory <0: if rate trajectory is negative, this implies that the intervals become increasingly longer with time and, therefore, interval j is longer than interval i and interval k is expected to be longer than interval j. In this case, the event window is lengthened, as shown in FIG. 4C, to accommodate the increasing intervals, but only to the extent of the inverse of the lower rate limit, which is shown as point Y in FIG. 4A.

3. Rate trajectory >0: if rate trajectory is positive, this implies that the intervals become increasingly shorter with time, and, therefore, interval j is shorter than interval i, and interval k is expected to be shorter than interval j. In this case, the event window is shortened, as shown in FIG. 4D, to accommodate the decreasing intervals, but only to the extent of the inverse of the maximum tracking rate, which is shown as point X in FIG. 4A.

This dynamic aspect of the event window allows for more natural increase and decrease of pacing rate. These concepts can also be analogously extended to atrial pacing applications.

Figure 4C:
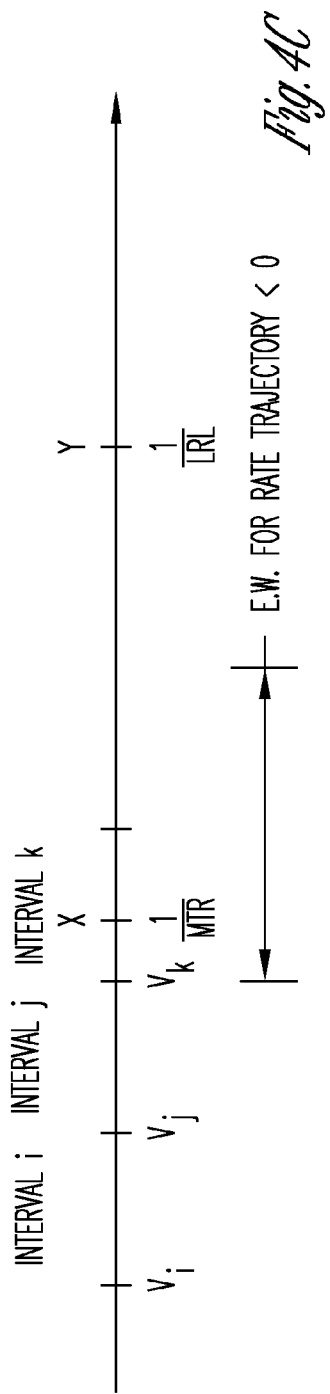
FIG. 4C demonstrates an event window (E.W.) for rate trajectory less than 0, according to one embodiment of the present system.
Figure 4D:
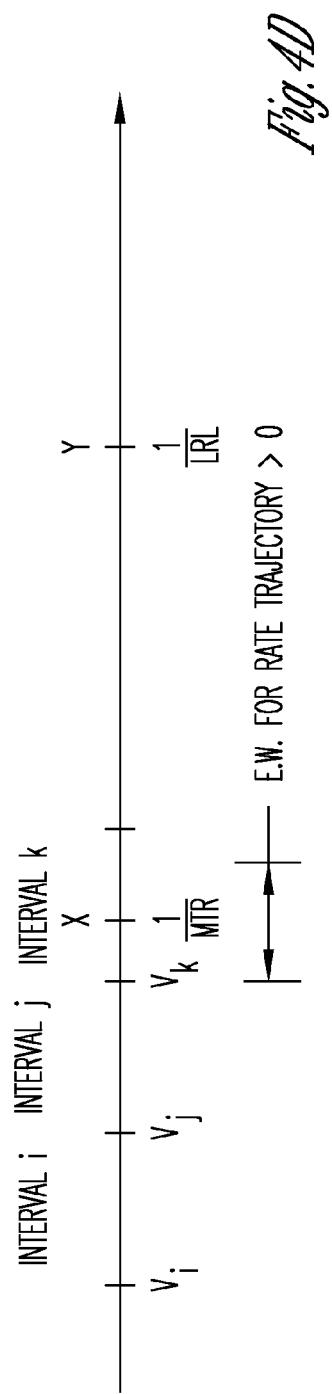
FIG. 4D demonstrates an event window (E.W.) for rate trajectory greater than 0, according to one embodiment of the present system.

If a ventricular contraction event not detected in any of the event windows of FIGS. 4B, 4C, and 4D, then the pacing device will be instructed to generate a ventricular contraction to prevent a long pause. In one embodiment, a ventricular contraction is generated by direct application of a pacing pulse to the ventricle. In one embodiment, a ventricular contraction is generated by a pulse to the atrium which propagates to the ventricle, but with an atrioventricular delay. For embodiments where the atrium is paced to provide a ventricular contraction, the event window may be shifted by an amount approximately equal to the atrioventricular delay. In such embodiments, the upper and lower limits of the event window are reduced by an amount approximately equal to the atrioventricular delay to account for the atrioventricular delay. This is one example of how the present concepts may be adapted to both single chamber and dual chamber pacing applications.

Several examples of equations used to generate event windows are provided in the following examples, which are intended to be demonstrative and not exhaustive or exclusive.

In one embodiment, the duration of the event window is described by the following equation:

$$\text{event window} = A - B^*(\text{heart rate}),$$

where (in one embodiment) A and B are constants. In one embodiment, A is the last V-V interval (or last A-A interval for atrial pacing).

In one embodiment, the duration of the event window is generated using both a plurality of previous intervals and by using rate trajectory, as demonstrated by the following equation:

$$\text{event window} = (\text{average over } N \text{ intervals}) - C^*d(\text{heart rate})/dT,$$

where N is an integer, C is a constant, and d(heart rate)/dT is rate trajectory.

In one embodiment, the duration of the event window is modified by the heart rate and derivative of the heart rate, as provided by the following equation:

$$\text{event window} = A - B^*(\text{heart rate}) - C^*d(\text{heart rate})/dT$$

where A, B, and C are constants, and d(heart rate)/dT is rate trajectory.

The system may be adjusted to deliver pacing pulses using higher or lower timing tolerances. To provide a more stringent pacing algorithm, the coefficients of the event window equation may be adjusted to make the event window conform more exactly to expected pacing rates. This may result in over pacing of the heart, however, such measures may be justified in circumstances where the patient is believed to be more susceptible to cardiac arrhythmia. To provide a less stringent pacing algorithm, the coefficients of the event window equation may be adjusted to allow more tolerance in the event window with respect to expected pacing rates. This will favor intrinsic pacing over forced pacing.

Another aspect of the present pacing system is that information other than rate information may be used to determine the sensitivity of the system and parameter values. For example, in one embodiment, sensors are used to determine the patient's conditions, such as exertion, elevated heart rate, or other activity. In situations where exertion, elevated heart rate, or other activity are known to cause cardiac arrhythmia, the event window generator may be programmed to provide more conservative and lower tolerance pacing to prevent long pauses, and potentially, cardiac arrhythmia. Sensors, such as minute ventilation detection systems and accelerometers, may be employed in this embodiment. In one embodiment, changes in amplitude of the minute ventilation signal represent depth of respirations and changes in frequency of the minute ventilation signal provide frequency of respiration. Other conditions may include autonomic balance, sympathetic activity characteristic of cardiac arrhythmia, parasympathetic activity characteristic of cardiac arrhythmia, sleep states, such as rapid eye movement (REM) sleep states, and transitions in sleep states. A timer may also be employed to provide conditions, such as, times of the day, week, month, year, and season, which are known factors in cardiac arrhythmia probabilities. Conditions also include circadian and ultradian trends. Times and trends may be based upon a population or an individual patient.

Figure 7:
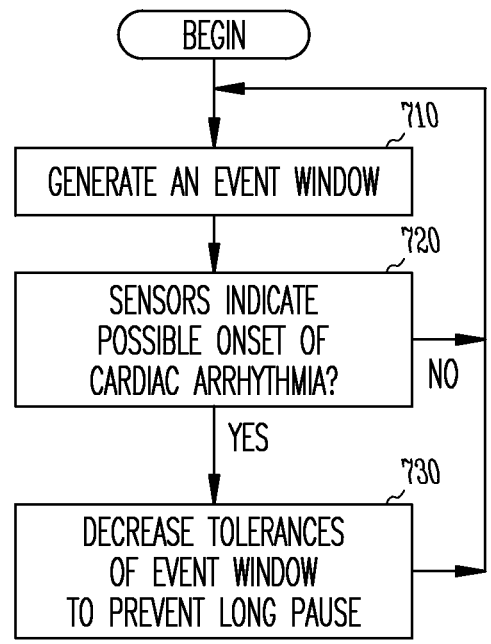
FIG. 7 is a flowchart demonstrating the use of the event window, according to one embodiment of the present system.

One example of such a system is shown in FIG. 7. In this system, the event window is generated using any of the concepts provided herein (710). The sensor information is used to identify conditions when increased sensitivity of the system would be beneficial to reduce the possibility of generation of long pauses (720). If such conditions arise, the event window is adjusted to provide less margin in pacing in order to reduce the possibility of a long pause (730). In one embodiment, the system is programmed to operate at the reduced margin until the conditions which initiated the reduced margin disappear. In one embodiment, the system is programmed to operate at the reduced margin for predetermined number of cardiac cycles. Other variations may exist within the scope of the present pacing system.

Figure 8:
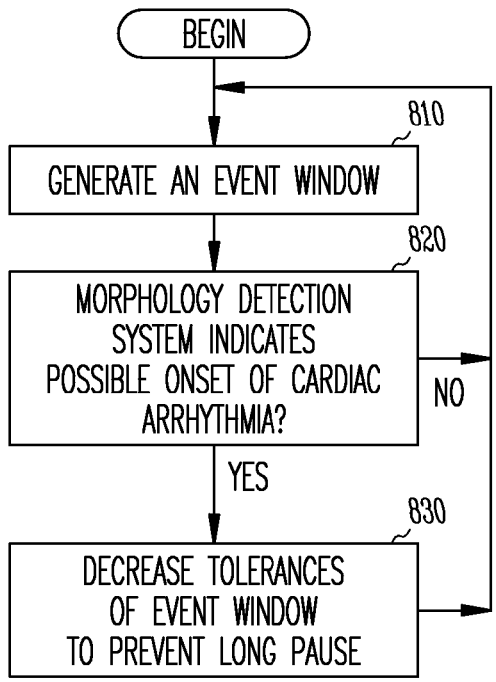
FIG. 8 is a flowchart demonstrating the use of the event window, according to one embodiment of the present system.

One embodiment employs a morphology detection system to detect abnormal morphologies in cardiac signals which may serve as triggers for the onset of cardiac arrhythmia. FIG. 8 shows one embodiment where an event window is generated by any of the concepts provided herein (810). Outputs from the morphology detection system are used to determine if abnormal morphologies are detected (820). Upon detection, the event window may be adjusted to decrease tolerances for better avoidance of long pauses. In one embodiment, the morphology detection circuit is used to identify complexes which deviate from a predetermined "normal" complex template, and thereby trigger increased sensitivity of the present pacing system (830). The morphological triggers may be tailored to a particular patient or based upon a population of patients. Such a system may also be used to acquire a database of morphological triggers, based upon a history for a patient.

It is contemplated that embodiments may use rate, sensor, and morphological outputs in various combinations to adjust the sensitivity of the event window generator. For example, priorities may be assigned to the various outputs, such that during particular conditions outputs may be selected from either the rate, sensor, or morphological outputs individually, depending on the accuracy of the information provided by each. For example, there may be situations where the sensors provide better predictors of possible onset of cardiac arrhythmia than the morphological detection system.

Figure 9:
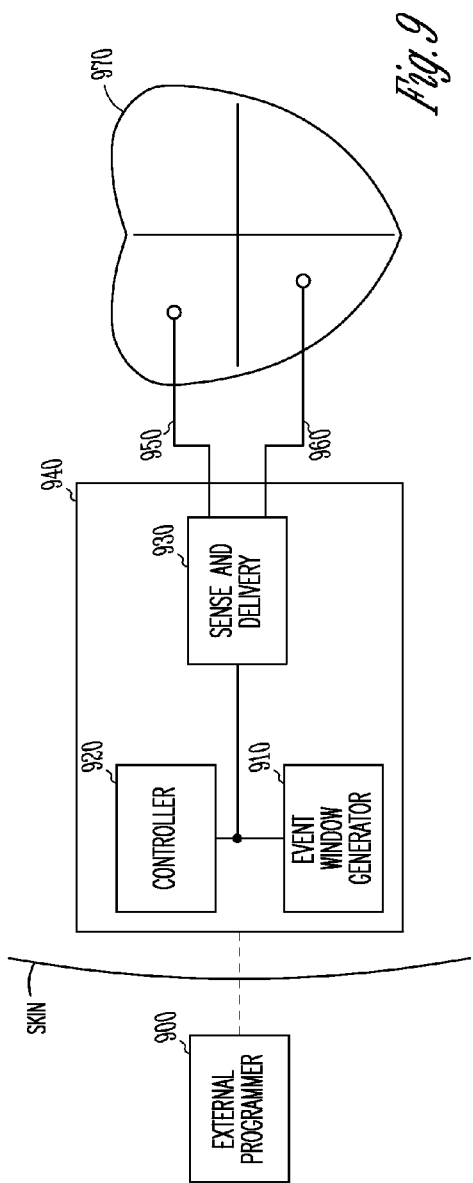
FIG. 9 is a block diagram of a pacing system with an event window generator, according to one embodiment of the present system.

One example of the cardiac pacing system, according to one embodiment of the present invention, is provided in FIG. 9. An external programmer 900 transmits instructions to an implanted pacing device 940 through the surface of skin. In this embodiment, atrial lead 950 and ventricular lead 960 measure signals from heart 970. Sense and delivery circuit 930 communicates with controller 920 and event window generator 910 to receive signals from, and deliver pulses to, the heart 970. It is noted that the present pacing system, in other embodiments, is an external pacing system with leads implanted in the heart 970. Other applications are possible without departing from the scope of the present system.

Figure 10:
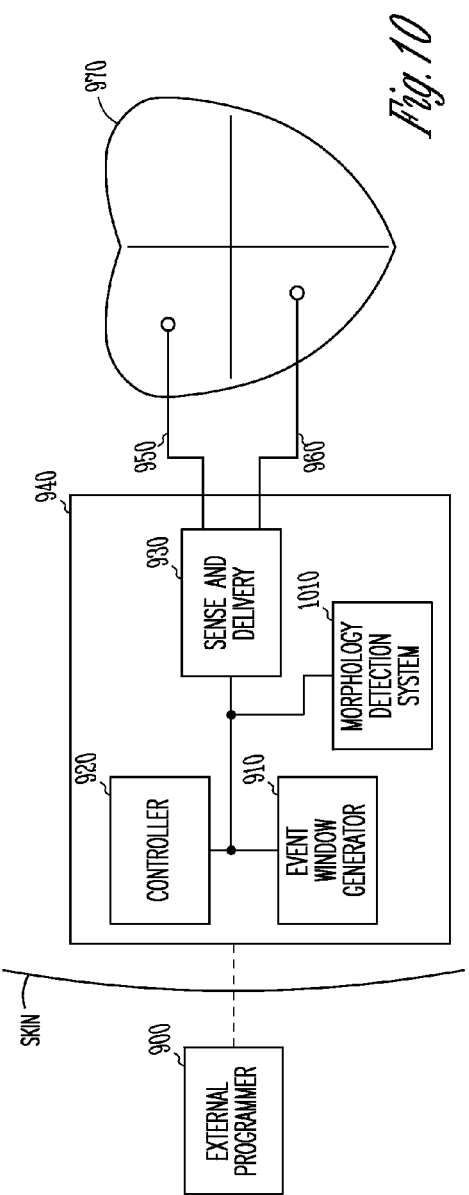
FIG. 10 is a block diagram of a pacing system with an event window generator and a morphology detection system, according to one embodiment of the present system.

FIG. 10 shows one embodiment of the pacing system of FIG. 9, with an added morphology detection system 1010. The event window generator 910 receives morphology detection information from morphology detection system 1010, and, in some embodiments, may adjust the event window accordingly as provided in this description.

Figure 11:
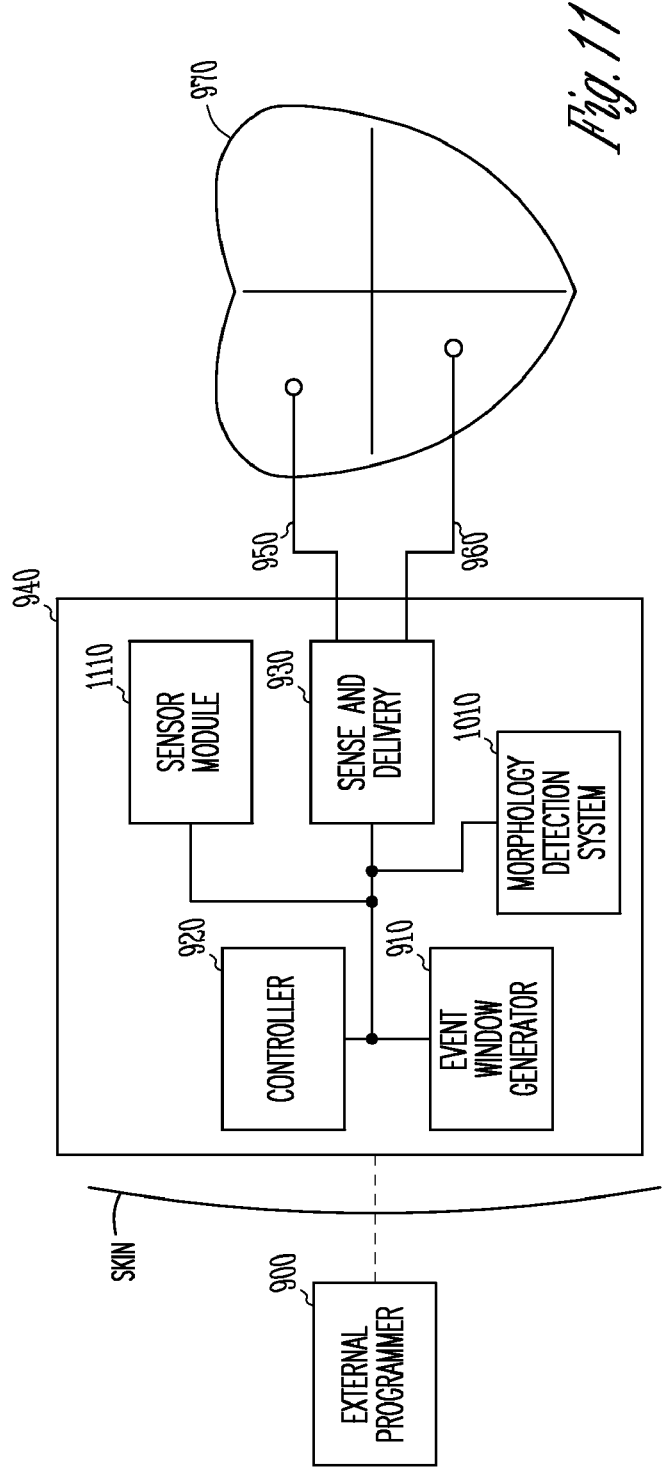
FIG. 11 is a block diagram of a pacing system with an event window generator, morphology detection system, and a sensor module, according to one embodiment of the present system.

FIG. 11 shows one embodiment of the pacing system of FIG. 10, with an added sensor module 1110. The event window generator 910 receives sensor conditions information from the sensors 1110, and, in some embodiments, may adjust the event window accordingly as provided in this description.

Although not shown, it is understood that the sensor module 1110 may be added to the system of FIG. 9. Therefore, the sensor module and morphology detection system are not necessarily practiced in the same embodiment with the event window generator, as shown in FIG. 11.

The systems of FIG. 9, FIG. 10, and FIG. 11 may be used for practicing the concepts provided herein for ventricular applications, atrial applications, and both ventricular and atrial applications. For ventricular pacing applications, it is possible to omit the atrial lead 950 in FIG. 9, FIG. 10, and FIG. 11. However, in such embodiments, to initiate ventricular contractions the pulse must be delivered directly to the ventricle via ventricular lead 960. For atrial pacing applications, it is possible to omit the ventricular lead 960 in FIG. 9, FIG. 10, and FIG. 11.

In the dual chamber embodiments, pause-preventing stimuli are synchronized to the previous ventricular contraction event. The time after each event is partitioned into two time epochs. During the first epoch, the device monitors cardiac activity but issues no stimuli. The duration of this epoch is determined by the current maximum stimulation rate (if a stimulus were issued before this time elapsed, the device would exceed the maximum stimulation rate). During the second epoch, electrical stimuli can be applied (they may be synchronized to atrial events detected during the first epoch). The duration of this epoch is determined by the difference between the cycle length corresponding to the current minimum stimulation rate and the cycle length corresponding to the current maximum stimulation rate. It is important to recognize that adjustments to the maximum stimulation rate affect both the first and second epoch durations. For example, if the maximum stimulation rate is reduced, the first epoch is lengthened and the second shortened (assuming that the minimum stimulation rate is unchanged).

Thus, the present event window system has improved ability to interrupt long pauses over that of rate smoothing. The present system provides embodiments having a more extensive history and context for rate determination; ectopic beats are often recognizable by intervals which are short in the context of the underlying rhythm. The present system allows for current rate trajectory estimation and may be used to flag deviations from the short-term trend for further analysis. For example, when rate is increasing progressively shorter intervals are expected and are not necessarily problematic but an interval which deviates significantly from the rate trajectory could potentially be malignant. Pacing pulses would be administered to maintain the observed heart rate trend (with some dynamic allowance for normal variability to avoid superfluous pacing). The concept may be employed during reduction in heart rate at the completion of exercise. These alterations guard against long pauses (and arrhythmia) resulting from premature beats evoked by the physical activity. Given the increasing prophylactic use of rhythm management devices in more active populations, this increased functionality is of value. Rate trajectory analysis may also be useful in preserving normal mechanisms of heart rate variability (e.g., respiratory sinus arrhythmia and baroreflex variations).

In addition to using a history of intervals, sensor information is also employed. For example, when a sensor or combination of sensors (accelerometer, minute ventilation, etc.) indicate that a period of increased activity has begun, the system can more closely scrutinize intervals and electrograms. This increased scrutiny is appropriate given the potentially increased arrhythmia risk due to increased sympathetic tone, concomitant reduced parasympathetic tone, and elevated circulating catecholamines. Other sources of information could be used to increase the system's scrutiny as well, including longer-term historical information about observed ectopy, elevated heart rate, exertion, or sympathetic balance (i.e., circadian and ultradian trends). In addition, knowledge of sleep and transitions and sleep state (particularly involving rapid eye movement, or REM, sleep—A detection scheme for this is already been disclosed for rhythm management devices) will also indicate appropriate measures for increased scrutiny. Simply increasing vigilance during certain times today may be useful (e.g., inspired by epidemiologic evidence of increased risk or sudden cardiac death in the early morning). Increased vigilance could consist of requiring that less stringent criteria be satisfied to trigger in intervention. For example, if both morphology and rate criteria are in use for abnormal beat detection, satisfaction of only one of the two criteria can result in system activation during times of elevated risk.

Beyond techniques already described, the system can also make use of morphology information accumulated throughout the life of the device. For example, a device which can recognize abnormal beats based on rate and morphology criteria (e.g., CCT or curvature-based classification) can substantially improve detection. Moreover, recognition of an arrhythmia trigger or marker (a sequence of undesirable beats associated with arrhythmia onset) initiates heightened scrutiny, pacing pulses to interrupt the sequence, and/or changes in the pacing regimen to suppress the sequences. Use of morphology information aids cases where rate zones might otherwise constrain behavior. By recognizing particular beats as normal or abnormal, the system can intervene with confidence even in tachy rate zones where rate smoothing is inhibited. Moreover, one embodiment of the system works irrespective of the previous interval length: when abnormal beats are observed, a lower rate limit is established to match the underlying rhythm.

In other embodiments, the system is also backed by additional device features which support and advocate its use. This can be accomplished not only by recognizing and trending short-long-short sequences as part of a diagnostic and trending framework, but also triggering electrograms (EGM) capture during the events. In addition, in some embodiments, short-long-short sequences are identified on episode EGMs to remind user that this phenomenon is preventable.

The system provides a new improvement over rate smoothing which is dynamic and adaptive. The new system identifies abnormal beats using rate and morphology information initiate's pacing thereafter, if necessary, to avoid a pause which may be conducive to arrhythmia. The system also uses historical and contextual information to adapt its behavior. This system will achieve suppression of short-long-short sequences without excessively constraining normal innocuous rate variations.

The foregoing examples are intended to demonstrate various aspects of the present pacing system, and are not intended in an exhaustive or exclusive sense. Variations in organization and construction of apparatus and order of method may exist without departing from the scope of the present invention, which is to be determined by the appended claims and their equivalents.

What is claimed is:

1. A system, comprising:
   a controller, connected to a sense and pulse delivery module, the controller receiving signals from one or more electrodes and providing pulse instructions for delivery of pulses to the one or more electrodes;
   an event window generator, connected to the controller, producing event windows for ventricular contraction events;
   one or more sensors connected to the controller; and
   a morphology detection system, connected to the controller, for detecting abnormal complexes,
   wherein the event windows are a function of ventricular rate and ventricular rate trajectory over a plurality of intervals between ventricular contraction events, signals from the one or more sensors, and information from the morphology detection system.

2. The system of claim 1, wherein the event windows are decreased for increases in ventricular rate trajectory.

3. The system of claim 2, wherein the event windows are increased for decreases in ventricular rate trajectory.

4. The system of claim 1, wherein the signals from the one or more sensors comprise signals indicative of one or more of physical exertion, elevated heart rate, circadian trends, and ultradian trends.

5. The system of claim 1, wherein the information from the morphology detection system comprises information on detection of arrhythmia trigger complexes.

6. The system of claim 5, wherein the event windows are decreased in response to the arrhythmia trigger complexes being detected.

7. The system of claim 1, wherein the information from the morphology detection system comprises information on detection of abnormal cardiac complexes.

8. The system of claim 7, wherein the event windows are decreased in response to the abnormal cardiac complexes being detected.

9. A system, comprising:
   a controller, connected to a sense and pulse delivery module, the controller receiving signals from one or more electrodes and providing pulse instructions for delivery of pulses to the one or more electrodes;
   one or more sensors, connected to the controller;
   a morphology detection system, connected to the controller, for detecting complexes indicative of cardiac arrhythmia; and
   an event window generator, connected to the controller, producing event windows for ventricular contraction events, the event windows each being a function of a plurality of intervals between ventricular contraction events and one or more of signals from the one or more sensors and signals from the morphology detection system,
   wherein the controller produces an instruction for providing a ventricular contraction following an event from which one of the event windows begins if a ventricular contraction event is not detected during the one of the event windows.

10. The system of claim 9, wherein the signals from the one or more sensors indicate conditions including one or more of physical exertion, elevated heart rate, circadian trends, and ultradian trends.

11. The system of claim 9, wherein, if the morphology detection system detects arrhythmia trigger complexes, the event window is decreased.

12. The system of claim 9, wherein, if the morphology detection system detects abnormal cardiac complexes, the event window is decreased.

13. The system of claim 9, wherein the event windows are each a function of a plurality of intervals between ventricular contraction events, a ventricular rate trajectory over the plurality of intervals between ventricular contraction events, and one or more of signals from the one or more sensors and signals from the morphology detection system.

14. The system of claim 13, wherein the event windows are decreased for increases in the ventricular rate trajectory.

15. The system of claim 13, wherein the event windows are increased for decreases in the ventricular rate trajectory.

* * * * *